United States Patent [19]

Schulte et al.

[11] Patent Number: 4,588,394
[45] Date of Patent: May 13, 1986

[54] INFUSION RESERVOIR AND PUMP SYSTEM

[75] Inventors: Rudolf R. Schulte, Santa Barbara; Gary P. East; Alfons Heindle, both of Goleta, all of Calif.

[73] Assignee: Pudenz-Schulte Medical Research Corp., Santa Barbara, Calif.

[21] Appl. No.: 590,349

[22] Filed: Mar. 16, 1984

[51] Int. Cl.⁴ .............................................. A61M 5/00
[52] U.S. Cl. ........................................... 604/9; 604/8
[58] Field of Search ...................................... 604/8–10, 604/175, 181, 183, 185, 186, 891

[56] References Cited

U.S. PATENT DOCUMENTS

| | | | |
|---|---|---|---|
| 342,131 | 5/1886 | Perkins et al. | 604/185 |
| 3,503,402 | 3/1970 | Schulte . | |
| 3,756,243 | 8/1973 | Schulte . | |
| 3,768,508 | 10/1973 | Schulte . | |
| 3,827,439 | 8/1974 | Schulte et al. . | |
| 4,360,019 | 11/1982 | Portner et al. | 604/891 |
| 4,364,395 | 12/1982 | Redmond et al. . | |

FOREIGN PATENT DOCUMENTS 0664424  6/1965  Belgium ................................. 604/9

OTHER PUBLICATIONS

Letter dated Dec. 21, 1983 from Dr. Robert R. Smith to Mr. Tom Sarro.
Drawing of the N.Y.U. Volume Control Valve.

Primary Examiner—C. Fred Rosenbaum
Assistant Examiner—Gene B. Kartchner
Attorney, Agent, or Firm—Pastoriza, Kelley & Lowry

[57] ABSTRACT

A totally subcutaneously implantable infusion reservoir and pump system includes a variable capacity reservoir for receiving and storing fluids containing medications for delivery to a catheter which directs the medications to a specific infusion location in the body. A pump and a valving arrangement is interposed between the reservoir and the catheter to facilitate and control the transfer of the medications from the reservoir to the catheter in a safe and efficient manner. In one preferred form, a normally closed first valve is situated between the reservoir and a pump, and a normally closed second valve is situated between the pump and the catheter in a manner such that the pump and valving arrangement defines a portion of a fluid flow conduit between the reservoir and the catheter. The pump and valving arrangement requires at least two deliberate and sequential steps before the medications stored in the reservoir can be transferred to the catheter. As an additional safety feature, an integral flow occluder can be added to the pump and valving arrangement to prevent the emptying of the medications in the reservoir through the catheter into the body when both normally closed valves are opened simultaneously. When the system is used in the treatment of terminally ill patients, the catheter can be placed within the body to direct morphine or other pain killing medications directly into the lateral ventricle of the brain or into the lumbar subarachnoid space.

110 Claims, 8 Drawing Figures

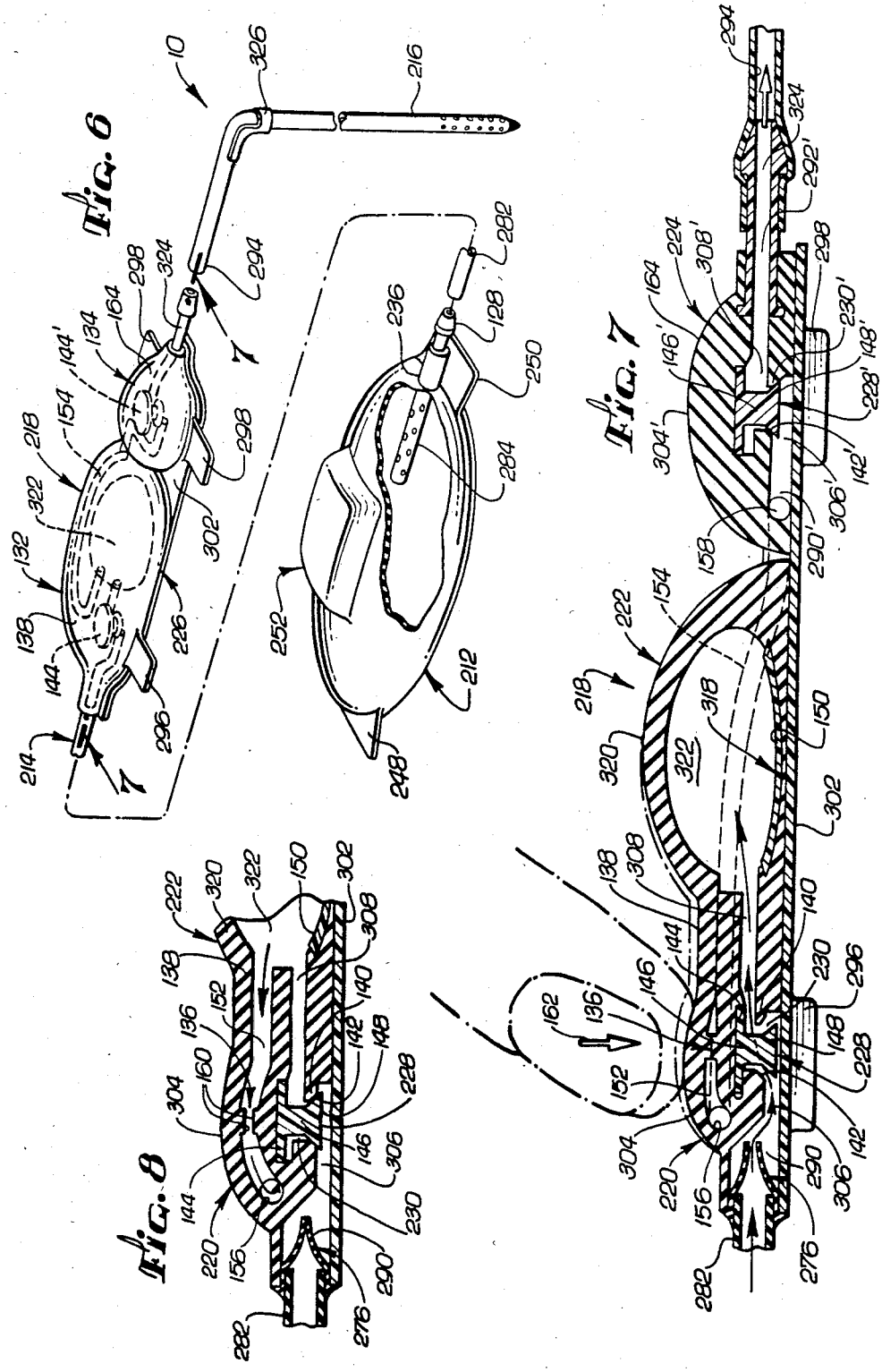

INFUSION RESERVOIR AND PUMP SYSTEM

BACKGROUND OF THE INVENTION

This invention relates generally to infusion systems for the administration of medications and, more particularly, to a refillable and subcutaneously implantable infusion reservoir and pump system useful for pain management in the treatment of terminally ill patients.

It has been found in the treatment of many terminally ill patients that the administration of various medications over sustained periods of time is necessary. For instance, it is often desirable to provide a pain killer, such as morphine, to such patients to help them cope with the sometimes excruciating pain which accompanies certain diseases. Frequently, terminally ill patients experience such extreme pain that hospitalization becomes necessary to provide the patient medications at intervals and in quantities sufficient to meet the patient's needs. Alternatively, when hospitalization is not acceptable, the patient is often required to obtain private nursing care.

Requiring a terminally ill patient to either be hospitalized or to arrange for private nursing care can result in substantial burdens being imposed upon both the health care system and the patient. Health care facilities are increasingly burdened as the demand for hospital bed space increases at a rate greater than the growth in available bed space. This burden is accentuated when patients, such as terminally ill patients, are hospitalized for want of an alternative treatment methodology. Also, the diversion of medically trained personnel to deal with the routine infusion of medications to terminally ill patients imposes additional burdens on the health care system which could be avoided, provided the proper technology were available.

When patients must be confined to a hospital bed or arrange for private duty nursing care to receive prescribed medications, the costs involved often exceed the financial means of such patients. For example, many terminally ill patients cannot afford to pay for the very expensive and individualized care which could make the last period of time prior to death much more productive and less difficult for the patient and for those around him. Indeed, many such patients cannot afford any medical care whatsoever and their only available alternative is to forego available treatments. Sometimes patients who cannot afford the hospitalization or private nursing care required and who cannot tolerate the pain involved with a particular disease must be hospitalized at society's expense.

These burdens to the patient, the health care system and to society in general have prompted several changes in health care methodology. For instance, many physicians have found it desirable to administer prescribed medications on an out-patient basis. This out-patient technique has proven to be effective in substantially reducing the costs associated in the treatment of many types of ailments; however, there have been a number of drawbacks which have made such out-patient arrangements less than ideal.

A typical drawback of out-patient treatment programs includes the requirement of frequent visits by the patient with the physician and the resultant time and transportation problems. It is generally recognized that if the patient could be provided adequate home care for extended periods of time, the time between visits with the physician could be lengthened. Such extended home care would benefit the physician, as well as the patient, in many circumstances by permitting the physician to devote more professional time to other important matters.

Notwithstanding the foregoing, some patients find that receiving regular injections of medications over a prolonged period of time is distasteful, not to mention painful. Additionally, it has been found that repeated injections through the skin into a specific, limited area of the body can be harmful to the patient and can sometimes cause problems which could become more threatening to the well-being of the patient than the illness being treated. Such problems have made necessary the use of alternate injection sites, the rotation of injections among alternate injection sites, or, at the extreme, the abandonment of medication injections as a useful form of treatment.

Moreover, some substances have been found to traumatize the skin when injected, and this has necessitated the use of alternate means for introducing such substances into the body. Such alternate introduction means have included the use of catheters which are inserted through the skin into the body and have a portion which remains extended through the patient's skin to provide external access. This and similar infusion systems have proven to be undesirable for extended treatment because of the risk of infection at the incision site where the catheter extends through the skin.

Accordingly, there has been a need in the medical arts for a system, including the appropriate devices, which allows the patient or his loved ones to administer required medications in precise quantities while minimizing the number of injections required and visits which need be made with a physician. Such a system should be constructed for total subcutaneous explacement in the body, include appropriate devices to prevent the unintended infusion of the medications into the body, and be refillable, such as by injection, to permit long term use. The present invention fulfills these needs and provides other related advantages.

SUMMARY OF THE INVENTION

The present invention resides in an infusion reservoir and pump system useful in the administration of medications to patients requiring infusions of medications at relatively frequent intervals and over extended periods of time. More particularly, the system is useful in the administration of pain killers directly into the central nervous system of terminally ill patients. In accordance with the present invention, the system, which can be totally subcutaneously positioned within the patient's body, generally includes a variable capacity reservoir which receives and stores the medications to be administered, a catheter which can be positioned to direct the medications to a selected portion of the patient's body, and a pump and valving arrangement useful for transferring the medications from the reservoir to the catheter and for preventing the unintended passage of the medications from the reservoir into the catheter for delivery to the patient.

In the illustrated embodiments, the reservoir supports an injection site apparatus capable of receiving the medications to be infused into the patient by injection. The injection site apparatus includes a self-sealing dome and a relatively rigid base which enclose an injection chamber. The injection site apparatus cooperates with an adjacent portion of the reservoir to permit the injected medications to flow from the injection chamber into the reservoir whenever the fluid pressure within the injection chamber exceeds the fluid pressure within the reservoir. This cooperation between the reservoir and the injection site apparatus also prevents the reverse flow of fluid from the reservoir to the injection chamber when the fluid pressure within the reservoir exceeds the fluid pressure within the injection chamber.

To control the direction of fluid flow through the system and to prevent any unintended infusion of medications into the patient, the illustrated embodiments require the fluid exiting the reservoir to flow through a one-way valve and a series of normally closed valves forming portions of a fluid flow conduit which directs the medications from the reservoir to the catheter. The normally closed valves are coactive with a pump to require specific and deliberated steps to pump the fluid containing the medications through the the system to the catheter for delivery to the patient. More specifically, the pump and valving arrangements of the illustrated embodiments require a deliberate and sequential, two-step procedure to fill and empty a pumping chamber within the pump. This procedure makes the inadvertent introduction of the medications into the patient highly unlikely.

To provide this safeguard, a normally closed first valve forms a portion of the fluid flow conduit between the reservoir and the pump. This first valve must be manually manipulated, as by percutaneous pressure when subcutaneously implanted, to permit the fluid medications to pass from the reservoir into the pump for filling the pumping chamber. A normally closed second valve is situated between the pump and the catheter to require a user of the infusion system to similarly manipulate the second valve to place the filled pumping chamber in open fluid communication with the catheter.

In one preferred form, the first and second valves are identical and they combine with the pump to form a single, integral control assembly unit. This control assembly unit forms a portion of the fluid flow conduit between the reservoir and the catheter, and the control assembly unit is remote from the one-way valve which is located within an outlet aperture of the reservoir. The first and second valves utilize flexible and resiliently biased valve diaphragms to generally overlie and close a valve aperture in each valve. These valve diaphragms can be displaced to uncover the valve apertures by applying percutaneous pressure to an overlying cover.

In another preferred form, the first valve provides a flow occluder which prevents the medications from exiting the pumping chamber while the first valve is opened. This flow occluder is an important safety feature of the system because it effectively prevents the emptying of the medications stored in the reservoir into the patient when both the first and second valves are opened. Also in this latter preferred form, the housings of the first and second valves are constructed of a resiliently flexible material, and each enclose a rigid valve stem extending through a valve passageway. This stem is normally biased to prevent flow through the valve passageway unless forceably displaced. Additionally, a one-way valve is located adjacent a first valve inlet to minimize fluid compression within the fluid flow conduit upstream the pump and also to prevent any fluid from exiting the first valve in any manner other than into the pumping chamber.

The catheter can be inserted into any portion of the body, such as the lateral ventricle of the brain or, alternately, into the lumbar subarachnoid space. In either configuration, the system provides an efficient and convenient apparatus and method for the administration of medications directly into the central nervous system of terminally ill patients. While such catheter placements are presently contemplated primarily to enhance the treatment of terminally ill patients, it is conceivable that the infusion reservoir and pump system of the present invention could be useful in other medical applications; for instance, in the administration of insulin to diabetic patients.

When the system of the present invention is surgically emplaced within a patient, it is deemed generally preferable to locate the reservoir near a softer area of the body where the skin can be manipulated to allow the reservoir to be percutaneously grasped. Typically, the reservoir will be located in a position remote from the catheter in the abdominal cavity, below the ribs, near a clavicle, or in any other suitable position the surgeon may choose. Besides forming a single, integral control assembly unit, the pump and valving arrangement can be constructed from separate, coactive components, each forming independent portions of the fluid flow conduit leading from the reservoir to the catheter. Notwithstanding the configuration of the pump and valving arrangement, it is preferable to locate each component generally adjacent a boney surface to provide the desired resistance to movement when the components are percutaneously manipulated. For instance, the pump and valving arrangement could be located adjacent a rib, a clavicle or an iliac crest depending on the insertion point of the catheter and the preferences of the surgeon.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a diagrammatic view of the alternate form of the present invention illustrated in FIG. 5, showing a portion of the reservoir shell broken away and the fluid flow path through the pump and valving arrangement in phantom for clarity;

FIG. 7 is an enlarged, fragmented sectional view of the pump and valving arrangement shown in FIG. 6, illustrating the manner in which a normally closed first valve is opened to permit the filling of a pumping chamber while simultaneously preventing the flow of fluid to a normally closed second valve through the provision of an integral flow occluder; and FIG. 8 is a fragmented sectional view of the normally closed first valve shown in FIG. 7, illustrating the configuration of the first valve in the absence of externally applied pressure.

DETAILED DESCRIPTION OF THE PREFERRED EMBODIMENT

Figure 1:
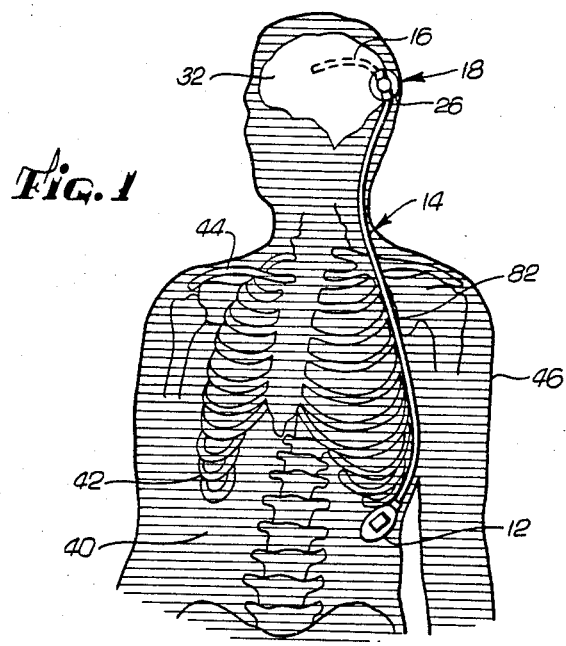
FIG. 1 is an environmental view of an infusion reservoir and pump system, illustrating exemplary subcutaneous locations of system components in a human body for the administration of medications directly into the lateral ventricle of the brain.

As shown in the drawings for purposes of illustration, the present invention is concerned with an infusion reservoir and pump system, generally designated by the reference number 10. This infusion reservoir and pump system 10 generally comprises a variable capacity reservoir 12 connected by a fluid flow conduit 14 to a catheter 16 which directs medications stored in the reservoir into the patient at a specific location. A pump and valving arrangement 18 is also provided to prevent or reduce the likelihood of an inadvertent infusion into the patient of medications stored in the reservoir 12.

It is generally deemed preferable that the system 10 be constructed for total subcutaneous implantation in the patient and that the variable capacity reservoir 12 be refillable by injection. The pump and valving arrangement 18 used in the system 10 can be situated between the reservoir 12 and the catheter 16 to form a portion of the fluid flow conduit 14 and the pump and valving arrangement can include one or more normally closed valves. Such a system would require fluid containing the medications to flow through the pump and valving arrangement 18 before passing into the catheter 16, and with the safety and well-being of the patient an all-important consideration in the employment of the system 10, this flow path requirement can provide the control over the flow of the medications which is critical to the system's safe use. Indeed, a pump and valving arrangement can be provided which practically eliminates the chance of inadvertently infusing more than a very small quantity of medication into the patient by requiring specific sequential and deliberate steps to be taken before a measured volume of fluid can be pumped through the system 10.

For example, to provide this safeguard a normally closed first valve 20 can be situated along the fluid flow path between the variable capacity reservoir 12 and a pump 22 to form a portion of the fluid flow conduit 14. This first valve 20 could be constructed to require manual manipulation, as by percutaneous pressure when subcutaneously implanted, to open the first valve and permit the fluid containing the medications to pass from the variable capacity reservoir 12 into the pump 22. A normally closed second valve 24 can be situated between the pump 22 and the catheter 16 to require a user of the system 10 to similarly manipulate the second valve for placing the pump in open field communication with the catheter.

Throughout this description and in the accompanying drawings, a prime symbol (') is used in connection with the reference numbers to identify elements of a second valve 24 and 224 which are functionally identical to corresponding elements of a first valve 20 and 220. Accordingly, in one preferred form of the present invention, the normally closed first and second valves 20 and 24 are functionally the same and they are combined with the pump 22 to form a single, integral control assembly unit 26. This control assembly unit 26 is situated along the fluid flow path between the reservoir 12 and the catheter 16 to form a portion of the fluid flow conduit 14. Each valve 20 and 24 includes a flexible and resiliently biased valve diaphragm 28 or 28' which generally overlies a valve aperture 30 or 30' and which can be displaced to open the valve to fluid flow. In another preferred form, a control assembly unit 226 includes an integral flow occluder 136 which prevents the medications from exiting a pump 222 and flowing to a second valve 224 while a first valve 220 is open. This integral flow occluder 136 adds an important safety feature to the system 10 because it effectively prevents the emptying of the reservoir 212 contents into the patient when both valves 220 and 224 are opened. Also in this latter preferred form, the valves 220 and 224 are constructed of a resiliently flexible material and the valves each house a rigid valve stem 228 or 228' extending through a valve passageway 230 or 230'. The valve stem 228 or 228' is normally biased to prevent flow through the valve passageway 230 or 230' unless forceably displaced.

The infusion reservoir and pump system 10 can substantially reduce the cost of treating some illnesses by eliminating the need for constant medical attention or by reducing the number of required visits which need be made with a physician. For instance, many terminally ill patients experience periods of extreme pain which require regular and frequent injections of morphine or other pain killing drugs. In many such cases, a patient having the system 10 implanted subcutaneously would be able to receive infusions of the required medications as needed while reducing the number of injections received as well as the number of out-patient visits with the responsible physician. The system 10 will also allow many patients to escape the confines of a hospital bed where the primary reason for the hospitalization is to provide access to the required amounts of medications. These benefits are possible because the variable capacity reservoir 12 can be sized to safely store a sufficient amount of medication to meet the patient's needs for a number of days.

Figure 5:
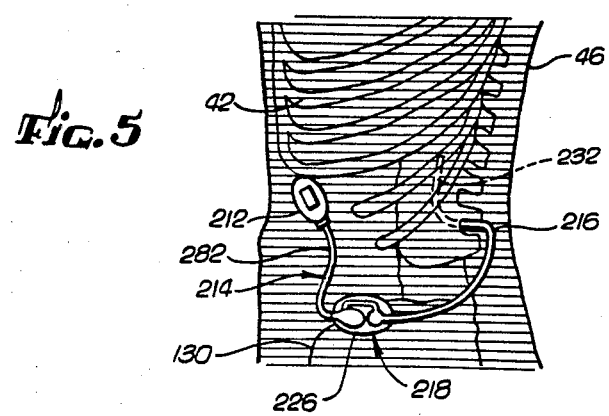
FIG. 5 is an environmental view of an alternate infusion reservoir and pump system, illustrating exemplary locations of system components in the human body for the administration of medications directly into the lumbar subarachnoid space.

By interposing the pump and valving arrangement 18 between the variable capacity reservoir 12 and the catheter 16 so that the pump and valving arrangement forms a portion of the fluid flow conduit 14, the danger of an inadvertent infusion of medication to the patient is reduced. Also, the overall design of the system 10 increases its utility for physicians and patients in that the system can be constructed in a variety of configurations for use in many types of different applications. For example, in the treatment of terminally ill patients, morphine can be injected into the lateral ventricle of the patient's brain 32 (FIG. 1) or into the lumbar subarachnoid space 232 (FIG. 5). Additionally, the system 10 may be used advantageously by patients requiring regular infusions of insulin due to diabetes by minimizing the number of injections received. Moreover, the inherent safety and utility of the infusion reservoir and pump system 10 will permit a patient's family or other loved ones to care for the patient in the privacy of the home and, particularly for terminally ill patients, make the period of illness much more productive and less difficult for the patient and those around him.

In accordance with the present invention, and as illustrated with respect to a first embodiment in FIGS. 1 through 4, the variable capacity reservoir 12 comprises a silicone elastomer shell 34 which can expand and collapse to accommodate changing volumes of fluid medications. The reservoir 12 includes an outlet aperture 36 through the shell 34 and a plurality of inlet apertures 38 generally situated through a portion of the reservoir shell remote from the outlet aperture. In systems 10 designed for use in the treatment of terminally ill patients, a reservoir 12 having a thirty milliliter capacity would normally hold sufficient amounts of morphine or other similar pain killing drugs to supply patients sufficient quantities of medications for several days. As illustrated in FIG. 1, the variable capacity reservoir 12 can be located in a remote position from the insertion point of the catheter 16 in any suitable position as the surgeon chooses, such as in the abdominal cavity 40, below the ribs 42 or near the clavicle 44. Indeed, the reservoir 12 can be placed in any soft area of the body 46 which would permit the reservoir to be percutaneously grasped while subcutaneously implanted. Attached to the reservoir shell 34 are a pair of suture tabs 48 and 50 which permit the surgeon to anchor the reservoir 12 at the selected location within the patient to prevent migration of the reservoir to an undesirable location.

An injection site apparatus 52 is provided which overlies the reservoir inlet apertures 38 and the adjacent portion of the reservoir shell 34. The injection site apparatus 52 includes a rigid base 54 and an overlying self-sealing dome 56 which enclose and define an injection chamber 58 therebetween. The self-sealing dome 56 is constructed of a silicone elastomer material, such materials providing acceptable levels of tissue reaction when subcutaneously implanted, which can be pierced by a twenty-five gauge or smaller needle 60 without affecting the ability of the dome to reseal after the needle has been withdrawn. The rigid base 54 can be constructed of a polypropylene or similar material to provide a needle-shield for the reservoir 12. The polypropylene material of the base 54 has sufficient rigidity to prevent the needle 60 inserted through the self-sealing dome 56 from piercing the shell 34 of the reservoir 12 and such material also provides acceptable levels of tissue reaction when subcutaneously implanted.

To provide an injection chamber exit passageway through the injection site apparatus base 54 and yet prevent the passage of an injection needle 60 through the base which could damage the underlying reservoir shell 34, the injection site apparatus base includes an integral, molded riser 62. This riser 62, best illustrated in FIG. 3, includes sidewalls 64 extending generally perpendicular to the plane of the base 54 toward the self-sealing dome 56, and a solid cap 66 perpendicular to and covering the sidewalls. The riser 62 extends from the inner surface of the base 54 into the injection chamber 58 to define a sub-chamber 68 between the injection chamber and the reservoir shell 34. A plurality of base apertures 70, forming needle-shield outlet passageways, are provided through the sidewalls 64 to permit medications injected into the injection chamber 58 to flow into the sub-chamber 68 while simultaneously preventing the needle 60 from passing through those base apertures and damaging the reservoir shell 34.

Generally surrounding the injection site apparatus base 54 is a flange 72 of the self-sealing dome 56. The underside of this flange 72 is securely attached to the reservoir shell 34 to connect the injection site apparatus 52 to the reservoir 12 while permitting the portion of the reservoir shell adjacent the injection site apparatus base 54 to move relative to that base. Importantly, this attachment permits the injection site apparatus base 54 to cooperate with the adjacent reservoir shell 34 to transfer fluid medications from the injection chamber 58 into the reservoir 12 when the fluid pressure within the injection chamber is greater than the fluid pressure within the reservoir.

Figure 3:
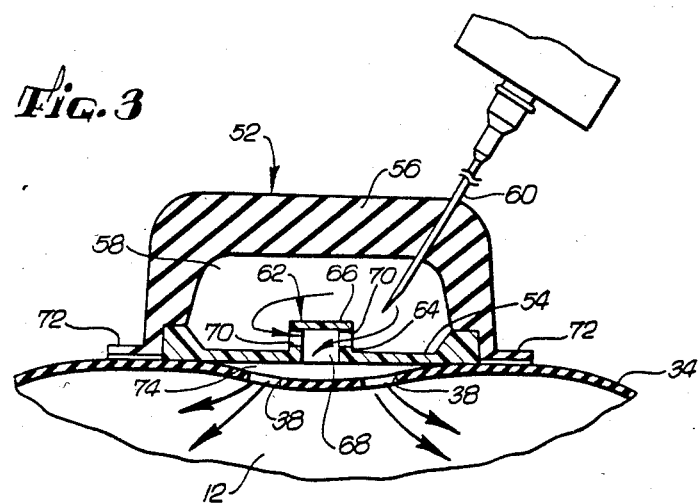
FIG. 3 is an enlarged, fragmented sectional view of an injection site apparatus and an adjacent portion of a variable capacity reservoir, illustrating the manner in which fluid containing medications is injected into an injection chamber and then flows from the injection chamber into the variable capacity reservoir when the fluid pressure within the injection chamber exceeds the fluid pressure within the variable capacity reservoir.

This fluid transfer is accomplished by positioning the reservoir inlet apertures 38 so they lie adjacent the underside of the injection site apparatus base 54 at a location removed from the injection site apparatus sub-chamber 68. The portion of the reservoir shell 34 adjacent the injection site apparatus base 54 is resiliently biased to normally lie flat against the injection site apparatus base to form a seal therebetween. By connecting the injection site apparatus 52 to the reservoir shell 34 at the self-sealing dome flanges 72, the portion of the reservoir shell adjacent the injection site apparatus base 54 can flex and separate from the injection site apparatus base sufficiently to provide a fluid passageway 74 between the sub-chamber 68 and the reservoir inlet apertures 38 (FIG. 3).

When the fluid pressure within the injection chamber 58 increases to a point where it exceeds the fluid pressure within the reservoir 12, the reservoir shell 34 adjacent the injection site apparatus base 54 flexes to separate from the base to permit the fluid to flow from the injection chamber through the injection chamber base apertures 70 into the sub-chamber 68, and from the sub-chamber through the reservoir inlet apertures 38 into the reservoir. After a sufficient amount of fluid medications have transferred from the injection chamber 58 to the reservoir 12 to equalize their respective fluid pressures, the resiliency of the portion of the reservoir shell 34 adjacent the injection site apparatus base 54 causes the reservoir shell to again lie flat against the underside of the injection site apparatus base. Because the reservoir inlet apertures 38 are caused to lie flat against the injection site apparatus base 54, the flow of fluid medications from the reservoir 12 into the injection chamber 58 is prevented even when the fluid pressure within the reservoir is greater than the fluid pressure within the injection chamber. This unidirectional flow feature provided by the cooperation between the injection site apparatus base 54 and the reservoir shell 34 provides a safety mechanism for the system 10 which prevents the escape of medications stored within the reservoir 12 through the injection site apparatus 52. This safety mechanism minimizes problems which could occur if medications began to leak through the self-sealing dome 56.

Figure 2:
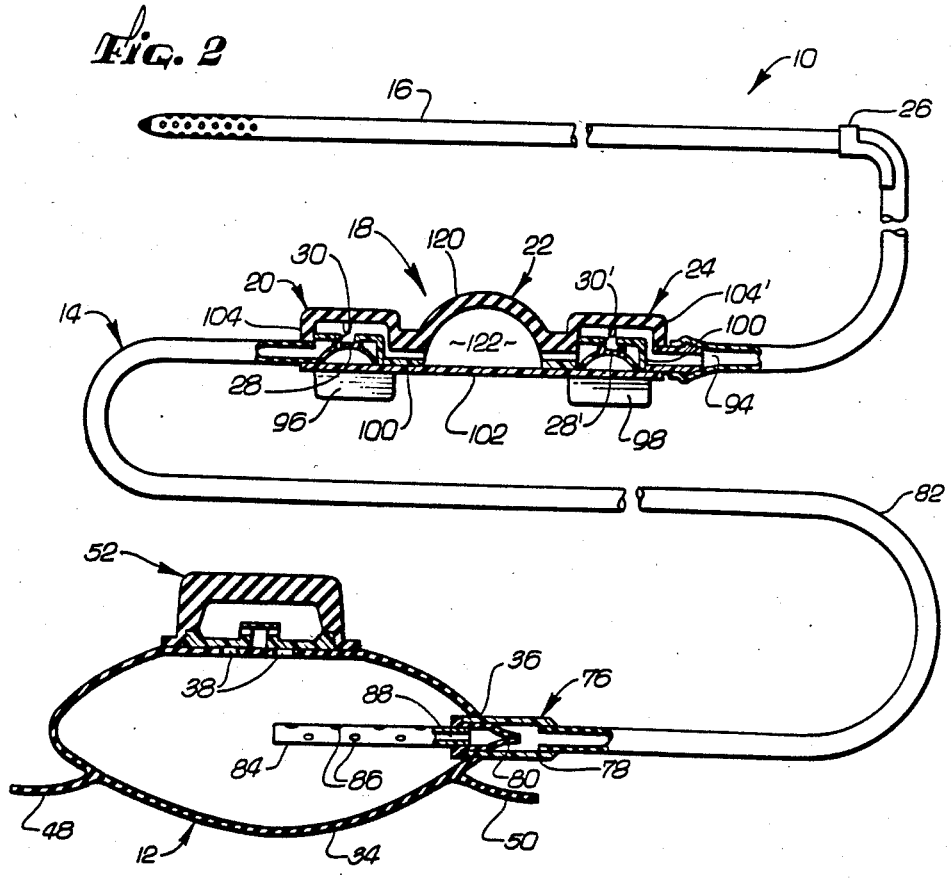
FIG. 2 is a diagrammatic and partially sectional view of one preferred form of the present invention.

A one-way valve 76 is situated within the reservoir outlet aperture 36 to allow fluid medications to flow from the reservoir 12 while preventing any fluids from entering the reservoir through the outlet aperture (FIG. 2). The one-way valve 76 includes a rigid encasement 78 which protects and supports an internal flexible valve membrane 80. The valve membrane 80 is fashioned after the well-known duck-bill or mitre valve, and the encasement 78 is preferably constructed of a polypropylene material to have sufficient rigidity to protect the valve membrane. The encasement 78 is integrally attached to a segment of surgical tubing 82 which forms a portion of the fluid flow conduit 14 directing the fluid medications from the reservoir to the catheter 16 for delivery to the patient.

A flexible tube 84 having a plurality of tube apertures 86 extends from the one-way valve encasement 78 generally rearwardly into the center of the reservoir 12. The flexible tube 84 is constructed preferably of a silicone elastomer material haing sufficient resiliency to maintain a flexible tube fluid passageway 88 through its center for channeling fluid medications from the reservoir 12 to the one-way valve 76 notwithstanding a collapse of the reservoir shell 34. Specifically, this flexible tube 84 is provide to insure the fluid medications will be able to exit the reservoir 12 even when the reservoir shell 34 collapses in a manner covering the reservoir outlet aperture 36. Such a collapse of the reservoir shell 34 may result from an emptying of fluid from the reservoir 12 during use of the system 10.

As the fluid medications are transferred from the reservoir 12 through the fluid flow conduit 14 to the catheter 16, the medications pass through the pump and valving arrangement 18. As illustrated in FIG. 2, the pump and valving arrangement 18 comprises an integral control assembly unit 26 which is attached to the surgical tubing 82 carrying fluid medications which have exited the reservoir 12 through the one-way valve 76. The control assembly unit 26 forms a portion of the fluid flow conduit 14 between the reservoir 12 and the catheter 16 and the unit is situated so that a unit inlet, which corresponds with a first valve inlet 90, is in open fluid communication with the reservoir outlet aperture 36, and a unit outlet, which corresponds with a second valve outlet 92', is in open fluid communication with a catheter inlet 94. The control assembly unit 26 includes generally the normally closed first and second valves 20 and 24 and the pump 22. The pump 22 is interposed in series between the first and second valves 20 and 24 so that the fluid medications must flow through each component of the control assembly unit 26 before exiting the unit for delivery to the catheter 16. The control assembly unit 26 is provided suture tabs 96 and 98 which allow the surgeon to anchor the unit in place when subcutaneously implanted to insure that it remains in the location selected by the physician.

The first and second valves 20 and 24 are normally closed to fluid flow in either direction and when these valves are subcutaneously implanted in a patient, they can be opened to fluid flow only when percutaneous pressure is selectively applied to the control assembly unit 26. Because percutaneous pressure must be applied to the unit 26 to open the valves 20 and 24 when subcutaneously implanted, it is preferable to locate the unit generally adjacent a bone, such as a clavicle 44 or a rib 42. Such a pump and valving arrangement 18 reduces the possibility of inadvertently infusing more than a small amount of medications into the patient because the control assembly unit 26 requires a combination of sequential and deliberate steps to pump the fluid medications through the system 10.

Each normally closed valve 20 and 24 includes a resiliently rigid housing 100 or 100' attached to an underlying support sheet 102, and a resiliently flexible cover 104 or 104'. A lower surface of the housing 100 or 100', which is preferably constructed of a polypropylene material, is securely attached to the underlying support sheet 102 in a manner creating a lower inlet chamber 106 or 106' in open communication with the valve inlet 90 or 90'. The underlying support sheet 102 can be constructed of any flexible material which produces acceptable levels of tissue reaction when subcutaneously implanted, such as reinforced silicon sheeting. The cover 104 or 104', which is preferably constructed of a silicon elastomer material, is securely attached to an upper surface of the housing 100 or 100' in a manner forming an upper outlet chamber 108 or 108' in open communication with the valve outlet 92 or 92'. An upper plate 110 or 110' of the housing 100 or 100' has the valve aperture 30 or 30' which permits the lower inlet chamber 106 or 106' to communicate with the upper outlet chamber 108 or 108'.

The flexible valve diaphragm 28 or 28', which is preferably formed of a silicone elastomer material, is supported within the lower inlet chamber 106 or 106'. The valve diaphragm 28 or 28' is generally constructed to form a dome-shaped member seated circumferentially upon the support sheet 102 in a manner resiliently biasing the valve diaphragm so that it is normally positioned over the valve aperture 30 or 30'. This valve diaphragm 28 or 28' is provided a plurality of diaphragm apertures 112 or 112' as well as a diaphragm ridge 114 or 114' which is molded onto the upper surface of the valve diaphragm 28 or 28' to engage the upper plate 110 or 110' in a manner surrounding the valve aperture 30 or 30' to form a seal which prevents any fluid flow through the valve aperture. Additionally, a knob 116 or 116' is provided on the underside of the cover 104 or 104' so that the knob is positioned generally directly above the valve aperture 30 or 30'.

Figure 4:
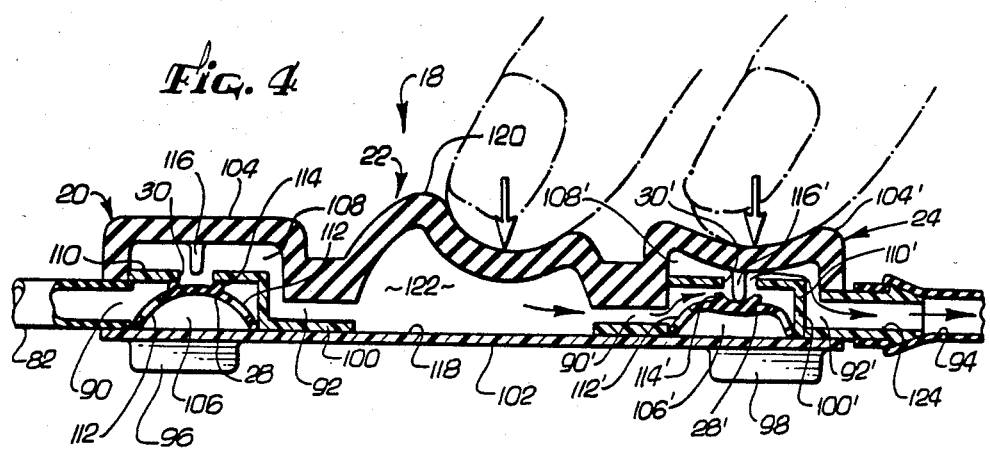
FIG. 4 is an enlarged, fragmented sectional view of the pump and valving arrangement shown in FIG. 2, illustrating the manner in which fluid is pumped through a normally closed second valve.

The knob 116 or 116' is situated for travel through the valve aperture 30 or 30' when the cover 104 or 104' is resiliently pressed downwardly, and the diameter of the knob is small enough to prevent the occlusion of the valve aperture when the knob is pressed therethrough. When enough pressure is applied, the knob 116 or 116' causes the valve diaphragm 28 or 28' to flex downwardly a sufficient distance to break the valve seal and allow fluids to pass through the valve aperture 30 or 30' (FIG. 4). The cover 104 or 104' and valve diaphragm 28 or 28' are each sufficiently resilient to return to their normal configurations and, consequently, close the valve 20 or 24 to fluid flow when the deforming pressure is removed from the cover. The inclusion of the normally closed valves 20 and 24 in the system 10 enhances the system's utility and safety by preventing the flow of fluids in either direction through the valves in the absence of direct and continuous external pressure.

The pump 22, which is interposed between the first valve outlet 92 and the second valve inlet 90', comprises a floor plate 118 and an overlying crown 120 which enclose and define a pumping chamber 122. The pumping chamber 122 preferably has an evacuation capacity of one milliliter, and the crown 120, which is resiliently biased to generally maintain a dome or arch-shape, can be deformed to lie substantially flat against the floor plate 118. The volume of the pumping chamber 122 can be customized to accommodate various intended uses of the system 10 and the required dosage to be infused into the patient per pumping stroke. The pump crown 120 is preferably constructed of a silicone elastomer material, and a portion of the reinforced silicone sheet 102 forms the pump floor plate 118. By constructing the pump crown 120 of a silicone elastomer material, medication can be injected, if necessary, directly into the pumping chamber 122 and the puncture site will tend to close upon itself and seal the pump crown when the needle 60 is removed.

While the pump and valving arrangement 18 is shown in the exemplary drawings as combined to form the single control assembly unit 26, the first valve 20, the second valve 24 and the pump 22 may be separately constructed to form individual system 10 components which can be connected to one another by a conduit such as the surgical tubing 82.

The catheter 16 is preferably formed of a barium-impregnated silicone elastomer material which is radiopaque for detection by X-ray photography. The catheter inlet 94 is attached to the second valve outlet 92' by sliding frictional engagement over a second valve outlet connector 124 integrally attached to the second valve 24. Fluid medications exiting the second valve outlet 92' immediately enter the catheter inlet 94 and are directed by the catheter 16 for infusion into a specific portion of the body 46. For example, in the case of terminally ill patients the catheter 16 can be inserted into the lateral ventricle of the patient's brain 32, as illustrated in FIG. 1. When such catheter 16 placement is contemplated, a catheter clip 126, as shown in FIG. 2, can be advantageously utilized to hold the catheter in place adjacent a burr hole through the skull.

The pump and valving arrangement 18 requires a two-step procedure to pump fluid medications from the reservoir 12 to the catheter 16. Before pumping may begin, however, the second valve cover 104' must be depressed to break the second valve seal and the pump crown 120 must be subsequently flattened to evacuate the pumping chamber 122 (FIG. 4). While the pump crown 120 is held in contact with the floor plate 118, the second valve cover 104' is released to permit the second valve diaphragm 28' to return to its normally closed position and thereby prevent any reverse fluid flow through the second valve 24 into the pumping chamber 122.

After this preparatory step has been completed and after the surgical tubing 82 has been primed with fluid medications, the pump 22 can be repeatedly transfer measured quantities of fluid from the reservoir 12 to the catheter 16 for infusion into the patient. To begin, the first step includes the depressing of the first valve cover 104 sufficiently to break the first valve seal. This permits fluid medications to flow from the first lower inlet chamber 106 through the first valve aperture 30 into the first upper outlet chamber 108 and then through the first valve outlet 92 into the pumping chamber 122. The biasing and resiliency of the pump crown 120 tends to draw the fluid medications through the first valve 20 to fill the pumping chamber 122 until the pump crown has resumed its dome or arch-shape. At times where the biasing and resiliency of the pump crown 120 is not sufficient to cause fluid flow through the system 10, the reservoir 12 can be percutaneously palpated to create adequate fluid pressure through the fluid flow conduit 14 to completely fill the pumping chamber 122.

After the pumping chamber 122 is filled with fluid medications, the first valve 20 is closed by simply releasing the first valve cover 104. This allows the resiliently biased first valve diaphragm 28 to again become positioned to block fluid flow through the first valve aperture 30. To transfer the fluid medications from the pumping chamber 122 through the second valve 24 to the catheter 16, the second step requires the second valve to be opened by depressing the second valve cover 104' to break the second valve seal. Once the second valve is opened, the pump crown 120 can be flattened to force substantially all of the fluid contained within the pumping chamber 122 through the second valve and into the catheter 16. Before releasing the pump crown 120, it is advisable to release the second valve chamber 104' to again close the second valve 24 fluid flow. This procedure prevents the suction of fluid from the catheter 16 through the second valve 24 and back into the pumping chamber 122 which could result from the natural tendency of the pump crown 120 to assume its dome or arch-shape.

It is evident from the foregoing that the sequential two-step pumping procedure prevents the inadvertent infusion of medications through the system 10 which could result in harm to the patient. The two-step procedure provides a safeguard for the system 10 even against indiscriminate application of percutaneous pressure to the control assembly 26. This infusion reservoir and pump system 10 can greatly ease the burden of medical personnel and hospital facilities by providing means for internally storing a large quantity of medication which is to be administered to a patient over an extended period of time. Various apparatuses can be added to the system 10 for a multitude of purposes, such as the provision of a burr hole reservoir situated adjacent the skull to facilitate injection of medications directly into the brain 32 while bypassing the pump and valving arrangement 18 of the system.

These foregoing features are enhanced and magnified in a second embodiment of the invention, illustrated in FIGS. 5 through 8, wherein functionally equivalent components common to the first and second embodiments are referred to in the drawings by corresponding reference numbers increased by two hundred. Generally, the second embodiment includes a variable capacity reservoir 212, an injection site apparatus 252 and a flexible tube 284 identical to the reservoir 12, the injection site apparatus 52 and the flexible tube 84 described in connection with the previous embodiment, with the exception that an integral reservoir outlet connector 128 is formed within the reservoir outlet aperture 236 rather than the one-way valve 76. The integral reservoir outlet connector 128 is designed to engage an inlet end of a segment of surgical tubing 282 to place the reservoir outlet aperture 236 in open fluid communication with the surgical tubing. This is accomplished by slidably inserting the reservoir outlet connector 128 into the inlet end of the surgical tubing 282 in a manner forming a friction seal between the reservoir outlet connector and the surgical tubing.

The second embodiment of the infusion reservoir and pump system 10 is very similar to the system described in connection with FIG. 2 in that both systems can be totally subcutaneously implanted within the patient and fluids can be injected into each injection site apparatus 52 and 252 to refill the attached variable capacity reservoir 12 and 212. In the second embodiment, the fluid medications flow from the reservoir 212 through the surgical tubing 282 to the pump and valving arrangement 218. The pump and valving arrangement 218 is constructed to form an integral control assembly unit 226 comprising a one-way valve 276 located within a normally closed first valve inlet 290, a normally closed first valve 220, a normally closed second valve 224, and a pump 222 interposed between the first and second valves. The first valve inlet 290 forms a control assembly unit inlet and a second valve outlet 292' generally corresponds with a control assembly unit outlet. From the second valve outlet 292', the fluids flows directly into a catheter 216 which can direct the fluid medications as described with respect to the catheter 16 of the first embodiment.

The locations of the individual components of the system 10 illustrated in FIGS. 5 through 8 should be selected by the surgeon as described in connection with the system components of the first embodiment. For example, when the catheter 216 supplied is intended to be inserted into the lumbar subarachnoid space 232, the surgeon will typically prefer to situate the control assembly unit 226 generally adjacent the iliac crest 130 to provide the desired backing support of a boney surface. The reservoir 212 and the injection site apparatus 252 will normally be situated in a soft portion of the body 46, typically near the rib cage 42, where the injection site apparatus is easily accessible for refilling the reservoir by injection. The control assembly unit 226 is situated between the reservoir outlet aperture 236 and the catheter inlet 294 to form a portion of the fluid flow conduit 214 and to provide positive control over the flow of medications through the system 10. To anchor the reservoir 212 and the injection site apparatus 252, a pair of reservoir suture tabs 248 and 250 are provided, and similarly, to anchor the control assembly unit 226 at a desired location, a pair of unit suture tabs 296 and 298 are provided.

As shown in FIG. 7, the control assembly unit 226 comprises generally an underlying reinforced silicone sheet 302 forming a unit base which supports a first sub-unit 132 including the one-way valve 276, the normally closed first valve 220 and the pump 222, and a second sub-unit 134 including the normally closed second valve 224. The first sub-unit 132 also includes an integral flow occluder 136 which automatically prevents any fluid transfer between a pumping chamber 322 and the second valve 224 when the first valve 220 is open. The one-way valve 276 is situated within the first valve inlet 290 to prevent the backflow of fluid medications from the first valve 220 into the surgical tubing 282.

As best illustrated in FIG. 8, the first sub-unit 132 includes a resiliently flexible first housing 138 attached to and overlying the reinforced sheet 302. The first housing 138 can be constructed of a silicone elastomer material in a manner permitting the first housing to reseal if punctured by a needle. A first housing inlet generally corresponds to the first valve inlet 290 and the unit inlet, and the first housing inlet internally receives and is fused to an outlet end of the surgical tubing 282 carrying fluid from the reservoir 212. Fluid flowing through the first housing inlet 290 initially enters a first lower inlet chamber 306 formed between the first housing 138 and the reinforced sheet 302. Fluid within the first inlet chamber 306 must await the opening of the first valve 220 before flowing into the pump 222. A first upper outlet chamber 308, which is in open fluid communication with the pump 222, is provided within the first housing 138. A portion of the first upper outlet chamber 308 is situated to generally overlie the first lower inlet chamber 306 so that a first valve passageway 230 through an intermediate portion 140 of the first housing 138 can provide a fluid flow path between the first lower inlet chamber and the first upper outlet chamber. The intermediate portion 140 of the first housing 138 generally surrounding this valve passageway 238 has a lower tapered surface which forms a first valve seat 142.

A generally T-shaped first valve stem 228 is provided within the first valve passageway 230 extending from the first upper outlet chamber 308 through the first valve passageway and into the first lower inlet chamber 306. This first valve stem 228 includes an upper expanded section 144 which is securely attached to an upper ceiling of the first upper outlet chamber 308 in a manner causing the first valve stem to move in response to any movement of that upper ceiling surface. The first valve stem 228 also includes a shaft 146 which extends downwardly from the upper expanded section 144 through the first valve passageway 230 and into the first lower inlet chamber 306 where this shaft enlarges slightly to form a first lower tapered foot 148 having a shape which cooperates with the taper of the first valve seat 142. In the normally closed position, as illustrated in FIG. 8, this first lower foot 148 contacts the first valve seat 142 to seal the first valve passageway 230 and prevent fluid flow between the first lower inlet chamber 306 and the first upper outlet chamber 308. The first upper outlet chamber 308 is also sufficiently large to accommodate movement of the upper expanded section 144 of the first valve stem 228 and still permit fluid flow therethrough. The first valve stem 228 is constructed of a material different from the material of the first housing 138 to reduce valve seat to valve stem sticking. For instance, the first valve stem 228 can be constructed of a polypropylene material to reduce the possibility of sticking to a silicone elastomer first valve seat 142 during storage, handling, shipping or use of the first valve 220.

The pumping chamber 322 is defined by an enlarged void created within the first housing 138. The first housing 138 provides the pump 222 with a resiliently flexible overlying crown 320 which can be manipulated by external pressure to flatten the crown against a pump floor 318 to cause evacuation of the pumping chamber 322. The pump floor 318 includes a needle-guard 150 which prevents a needle tip, which may be inserted through the pump crown 320, from passing through the pump floor.

The first housing 138 also includes a first housing outlet 152 which forms a pump outlet passageway generally overlying the first upper outlet chamber 308. This first housing outlet 152 is in open communication with a control assembly unit connector tube 154 which directs the fluid exiting the first housing 138 to a second housing inlet 290'. The connector tube 154 is integrally attached to the first housing 138 at a first housing outlet port 156 and to the second sub-unit 134 a second housing inlet port 158.

Situated within the first housing outlet 152 between the pumping chamber 322 and the first housing outlet port 156 is the integral flow occluder 136 which generally includes a pair of spaced apart, cooperating boots 160 which, when pressed together, prevent fluid flow through the first housing outlet. This flow occluder 136 is positioned directly above the first valve stem 228 along its longitudinal axis, the first lower inlet chamber 306, the first valve passageway 230, and the first upper outlet chamber 308.

As illustrated in FIG. 8, when the first valve 220 is in its normally closed configuration, fluid cannot pass from the first lower inlet chamber 306 to the first upper outlet chamber 308 because a seal is formed between the first lower foot 148 and the first valve seat 142. The pumping chamber 322 is in open fluid communication with the first housing outlet port 156 through the first housing outlet 152 because the cooperating boots 160 of the integral flow occluder 136 are spaced to permit fluid flow therethrough. This configuration is maintained by natural resiliency and biasing constructed into the first housing 138. When external pressure is applied downwardly to the first housing 138 at a point overlying the first valve 220, as illustrated by the arrow 162 in FIG. 7, a first housing upper cover 304 is forced downwardly to cause the boots 160 of the flow occluder 136 to meet and close the first housing outlet 152 to fluid flow. Furthermore, as the downward pressure on the first housing upper cover 304 is increased, the upper ceiling of the first upper outlet chamber 308 is deformed and moved downwardly, causing an equivalent downward movement of the first valve stem 228. As the first valve stem 228 is moved downwardly, the seal between the first lower foot 148 and the first valve seat 142 is broken, placing the first lower inlet chamber 306 in open fluid communication with the first upper outlet chamber 308.

This construction of the first housing 138 to include the flow occluder 136 adds an important safety feature to the infusion reservoir and pump system 10 because there can never be more than the volume of fluid contained within the pumping chamber 322 which can pass from the first sub-unit 132 to the second sub-unit 134 each time the first valve seal is broken. Whenever the first valve 220 is opened, the flow occluder 136 blocks the first housing outlet 152 to fluid flow and thus prevents any fluid medications from exiting the pumping chamber 322 and flowing to the second valve 224. With the fluid flow conduit 214 so blocked, the second valve 224 can be simultaneously opened with the opening of the first valve 220 without placing the reservoir 212 in open communication with the catheter 216 and risking an excessive transfer of medications through the system 10.

The second sub-unit 134 is functionally and structurally very similar to the first sub-unit 132 with the exception that it is simplified to include only the normally closed second valve 224. The second sub-unit 134 comprises a resiliently flexible second housing 164 generally overlying the reinforced sheet 302. The second housing 164 forms a second lower inlet chamber 306' and an overlying second upper outlet chamber 308' which communicate with each other through a second valve passageway 230' in a manner very similar to that described in connection with the first sub-unit 132. A second valve stem 228', which is identical to the first valve stem 228, is provided to form a second valve seat between a second lower foot 148' and a second valve seat 142' in a manner similar to that described in connection with the first valve 220. In fact, the second valve 224 is structurally the same as the first valve 220.

The second lower inlet chamber 306' is in open communication with the second housing inlet 290' which, in turn, is in open fluid communication with the connector tube 154. Forming a portion of the second upper outlet chamber 308' is an integral outlet connector 324 which defines the control assembly unit outlet. As was the case with the first valve 220, the natural resiliency and biasing of the second housing 164 holds the second valve 228' in a position where the second lower foot 148' interacts with the second valve seat 142' to prevent fluid flow through the second valve passageway 230'. The second valve seal can be broken by applying downward pressure to a second housing upper cover 304' of the second housing 164 with sufficient force to cause the downward movement of the second valve stem 228' through the second valve passageway 230' to break the second valve seal. When the second valve seal is broken, the second lower inlet chamber 306' is placed in open fluid communication with the second upper outlet chamber 308'.

The reinforced sheet 302 underlying the first and second housings 138 and 164 is sufficiently flexible to facilitate positioning of the control assembly unit 226 within the body 46 to follow the body's natural contours. The first and second housings 138 and 164 are separately attached to the reinforced sheet 302 and they are structurally independent of one another to also further enhance this contouring quality of the control assembly unit 226. In a manner similar to that described in connection with the previous embodiment, the first and second sub-units 132 and 134 could easily be separated for individual placement within the patient. All that would be required to effect such a separation would be to lengthen the connector tube 154 which channels the fluid medications from the first housing outlet port 156 to the second housing inlet port 158.

The catheter 216 illustrated in FIG. 6 is identical to the catheter 16 previously described and illustrated in FIG. 2. The catheter clip 326 illustrated is useful for positioning the catheter 216 when it is inserted into the lateral ventricle of the patient's brain 32, and this catheter clip can be deleted, for example, when the system 10 is to be used to infuse medications into the lumbar subarachnoid space 232 (FIG. 5).

To transfer medications from the reservoir 212 to the catheter 216, the control assembly unit 226 requires a two-step procedure to be followed. Before this two-step procedure can begin, however, the pumping chamber 322 must be evacuated of all fluids in a manner causing the pumping crown 320 to be flattened against the needle-guard 150. The surgical tubing 282 connecting the reservoir 212 to the first sub-unit 132 must also be primed with the fluid medications.

Once these preliminary tasks have been accomplished, the first step of the pumping procedure can be initiated by depressing the first housing upper cover 304 overlying the first valve 220 in the direction indicated by the arrow 162 in FIG. 7. Such depression of the first housing cover 304 causes the integral flow occluder 136 to block the escape of fluid from the pumping chamber 322 to the first housing outlet port 156, and the downward movement of the first valve stem 228 breaks the first valve seal allowing fluid to pass from the first lower inlet chamber 306 to the first upper outlet chamber 308 and into the pumping chamber 322. The natural resiliency of the pump crown 320 tends to draw fluid through the first valve 220 as the pumping chamber 322 expands until the pump crown 320 has attained its natural dome or arch-shape. Throughout this first step the fluid medications are restricted to flowing past the one-way valve 276, through the first valve 220 and into the pumping chamber 322.

After the pumping chamber 322 has been filled with the fluid medications, the external downward pressure exerted upon the first housing upper cover 304 is released. This removal of downward pressure allows the natural resiliency and biasing of the first housing 138 to move the first valve stem 228 upwardly to close the first valve 220 and also to space the boots 160 of the flow occluder 136 to place the pumping chamber 322 in open fluid communication with the second housing inlet 290'.

To begin the second step of the pumping operation, the second housing upper cover 304' is pressed downwardly to break the second valve seal. After the second valve seal has been broken, the pumping chamber 322 can be evacuated through the first housing outlet 152 by simply depressing the pump crown 320 downwardly until it is flattened against the needle-guard 150. The fluid medications contained within the pumping chamber 322 will flow through the first housing outlet 152 past the spaced apart boots 160 of the flow occluder 136 and into the connector tube 154 which carries the medications to the second housing inlet port 158. From the second housing inlet port 158, the fluid medications flow into the second lower inlet chamber 306', through the second valve passageway 230' past the second valve stem 228', and into the second upper outlet chamber 308' where the fluid is placed in open fluid communication with the catheter 216.

After the pumping chamber 322 has been so evacuated, it is generally deemed preferable to sequentially remove the pressure exerted on the second housing cover 304' to allow the second valve 224 to reseal and then release the downward pressure on the pump crown 320. This sequence is preferable because if the pump crown 320 was released prior to closing the second valve 224, the natural resiliency and biasing of the pump crown would tend to suck fluid from the catheter 216 through the second valve back into the pumping chamber 322 as the resilient pump crown resumed its natural arch or dome-shape and the volume of the pumping chamber expanded.

The flow occluder 136 of the control assembly unit 226 greatly enhances the utility and safety of the system 10 because even if both normally closes valves 220 and 224 were simultaneously opened, there would be no inadvertent infusion of medication into the patient. The natural resiliency of the first and second housings 138 and 164 causes the first and second valve stems 228 and 228' to form seals sufficiently strong to prevent flow in either direction through the first and second valves 220 and 224. However, if the first and second housings 138 and 164 were constructed of a material having less than ideal natural resiliency, a hole could be provided in the bottom of each valve stem 228 and 228' which could position a spring and plunger arrangement which would interact with the reinforced sheet 302 to enhance the tendency of the valve stems to move upwardly. Also, it is deemed generally preferable that the system 10 be constructed with as few connections as possible to minimize the possibility of leakage through the fluid flow conduit 214.

It is evident from the foregoing that both disclosed embodiments of the infusion reservoir and pump system 10 can be beneficially used by patients to reduce medical costs associated with the treatment of illnesses requiring frequent injections. Various apparatuses can be added to the systems 10 without detracting from their basic utility. Also, it is evident that the systems 10 provide means for safely and efficiently transferring measured quantities of medications simply through percutaneous palpation of the pump and valving arrangements 18 and 218.

Although two particular embodiments of the invention have been described in detail for purposes of illustration, various modifications may be made to each without departing from the spirit and scope of the invention. Accordingly, the invention is not to be limited, except as by the appended claims.

We claim:
1. A normally closed valve for use in an infusion reservoir and pump system, said valve comprising:
   a resiliently flexible housing having an inlet and an outlet;
   an inlet chamber within said housing, said inlet chamber being in open communication with said inlet;
   an outlet chamber within said housing, said outlet chamber generally overlying said inlet chamber and said outlet chamber being in open communication with said outlet;
   a valve passageway through said housing between said inlet chamber and said outlet chamber, the portion of said housing generally surrounding said valve passageway forming a valve seat; and
   a valve stem attached to and extending downwardly from an upper ceiling of said outlet chamber through said valve passageway and into said inlet chamber, said valve stem including a lower foot which sealingly engages said valve seat, the seal being replaceably broken when a housing cover overlying said outlet chamber is resiliently deformed to cause the downward movement of said valve stem through said valve passageway.

2. A valve as recited in claim 1 wherein said housing is constructed of a silicone elastomer material.

3. A valve as recited in claim 1 wherein said valve stem is constructed of a polypropylene material.

4. A valve as recited in claim 1 wherein said inlet chamber is defined, in part, by a reinforced sheet underlying said housing.

5. A valve as recited in claim 1 including an integral, rigid connector defining said outlet.

6. A valve as recited in claim 1 including a pumping chamber interposed between said outlet chamber and said outlet, said pumping chamber being defined generally by a hollow void created within said housing in a manner providing a resiliently flexible crown over said void which can be depressed to flush fluid from said pumping chamber.

7. A valve as recited in claim 6 including a rigid needle-guard forming a floor for said pumping chamber, said needle-guard preventing a needle which may be inserted through said crown from passing through said floor of said pumping chamber.

8. A valve as recited in claim 1 including means for occluding said outlet when said housing cover is resiliently deformed to cause the downward movement of said valve stem through said valve passageway.

9. A subcutaneously implantable infusion reservoir and pump system, comprising:
   means for receiving medication into said system by injection when said system in subcutaneously implanted;
   a reservoir securely attached to said receiving means in a manner permitting the subcutaneous transfer of medication from said receiving means to said reservoir, said reservoir including a reservoir outlet;
   a catheter for directing the medication to a specific location in a body removed from said reservoir, said catheter having a catheter inlet and being positionable within the body independently of the position of said reservoir;
   means for subcutaneously conducting the medication from said reservoir outlet to said catheter inlet; and
   means for pumping and controlling the flow of medication from said reservoir to said catheter, said pumping and controlling means forming a portion of said conducting means and including normally closed valve means and a pump which is separated from said reservoir outlet and said catheter inlet by other portions of said conducting means.

10. A system as recited in claim 9 wherein said pump includes a pump inlet, a pump outlet, and a resilient crown overlying a floor plate to define a pumping chamber therebetween, said pump being actuated through manual percutaneous pressure applied to said resilient crown, when subcutaneously implated.

11. A system as recited in claim 10 wherein said receiving means includes a self-sealing dome overlying a rigid needle-shield to define an injection chamber therebetween, said needle-shield having a shield outlet passageway to permit the outflow of medication from said injection chamber into said reservoir through a reservoir inlet when the fluid pressure in said injection chamber exceeds the fluid pressure in said reservoir.

12. A system as recited in claim 11 wherein said reservoir inlet is resiliently biased to be normally situated adjacent an undersurface of said needle-shield, said reservoir inlet separating from said undersurface when the fluid pressure within said injection chamber is greater than the fluid pressure within said reservoir to allow fluid flow through said shield outlet passageway to said reservoir inlet.

13. A system as recited in claim 11 wherein said reservoir includes a flexible outer body capable of expanding to accommodate varying amounts of medication.

14. A system as recited in claim 13 further including a flexible tube extending from said reservoir outlet into said reservoir to channel fluids through said reservoir outlet notwithstanding a collapse of said reservoir about said reservoir outlet.

15. A system as recited in claim 10 including a one-way valve situated within said conducting means, said one-way valve causing fluid flow through said conducting means to be unidirectional.

16. A system as recited in claim 15 wherein said one-way valve is situated adjacent said reservoir outlet and includes a rigid encasement which protects a resilient one-way valve membrane situated within said encasement.

17. A system as recited in claim 10 wherein said catheter is constructed of a radiopaque, bariumimpregnated silicone elastomer material.

18. A system as recited in claim 9 wherein said normally closed valve means includes a normally closed first valve positioned between said reservoir and said pump.

19. A system as recited in claim 18 wherein said normally closed valve means further includes a normally closed second valve positioned between said pump and said catheter inlet.

20. A system as recited in claim 19 wherein said first valve includes a rigid first housing and a resilient first cover, said first housing forming a first lower inlet chamber which houses a flexible first valve diaphragm resiliently biased to close a first valve aperture through said first housing, and said first cover including means for displacing said first valve diaphragm away from said first valve aperture to open said first valve.

21. A system as recited in claim 20 wherein said second valve includes a rigid second housing and a resilient second cover, said second housing forming a second lower inlet chamber which houses a flexible second valve diaphragm resiliently biased to close a second valve aperture through said second housing, said second cover including means for displacing said second valve diaphragm away from said second valve aperture to open said second valve.

22. A system as recited in claim 20 wherein said displacing means includes a first knob attached to a lower surface of said first cover, said first knob being positioned to pass through said first valve aperture to displace said first valve diaphragm when said first cover is pressed downwardly, the displacement of said first valve diaphragm allowing the medication to pass from said first lower inlet chamber through said first valve aperture into a first upper outlet chamber, said first upper outlet chamber being in fluid communication with said pump.

23. A system as recited in claim 10 wherein said normally closed valve means comprises:
a resiliently flexible housing having an inlet and an outlet;
an inlet chamber within said housing, said inlet chamber being in fluid communication with said inlet;
an outlet chamber within said housing, said outlet chamber being in fluid communication with said outlet and said outlet chamber generally overlying said inlet chamber;
a valve passageway through said housing between said inlet chamber and said outlet chamber, an intermediate portion of said housing generally surrounding said valve passageway and being tapered to form a valve seat; and
a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway.

24. A system as recited in claim 23 wherein said pump is interposed between said outlet chamber and said outlet, said pump being defined generally be a hollow void created within said housing, said void forming said pumping chamber.

25. A system as recited in claim 24 wherein said floor plate forms a rigid needle-guard, said needle-guard preventing a needle which may be inserted through said crown from passing through said floor plate.

26. A system as recited in claim 23 including means for occluding said pump outlet and thereby preventing flow through said pump outlet when said upper cover portion of said housing overlying said outlet chamber is resiliently deformed to cause the downward movement of said valve stem through said valve passageway.

27. A subcutaneously implantable control assembly for use in an infusion reservoir and pump system, said assembly comprising:
a rigid housing and a resiliently flexible cover over said housing, said housing and said cover cooperating to substantially enclose and define a fluid flow passageway through said assembly;
a normally closed first valve formed at least in part by said housing and said cover, said first valve having a first valve inlet and a first valve outlet;
a pump having a pump outlet, a pump inlet in fluid communication with said first valve outlet, and a resilient crown formed at least in part by said cover and defining at least a portion of a pumping chamber; and a normally closed second valve formed at least in part by said housing and said cover, said second valve having a second valve inlet and a second valve outlet, said second valve inlet being in fluid communication with said pump outlet;

said valves being opened and said pump being actuated by the selective application of percutaneous manual pressure to said cover when said assembly is subcutaneously implanted.

28. An assembly as recited in claim 27 wherein said housing forms a first lower inlet chamber in said first valve, said first lower inlet chamber supporting a first valve diaphragm resiliently biased to close a first valve aperture through said housing.

29. An assembly as recited in claim 28 wherein said housing forms a second lower inlet chamber in said second valve, said second lower inlet chamber supporting a second valve diaphragm resiliently biased to close a second valve aperture through said housing.

30. An assembly as recited in claim 29 wherein said cover includes means for displacing said first valve diaphragm away from said first valve aperture and said second valve diaphragm away from said second valve aperture.

31. An assembly as recited in claim 30 wherein said displacing means includes a first knob attached to a lower surface of said cover, said first knob being positioned to pass through said first valve aperture to displace said first valve diaphragm when said cover is pressed downwardly.

32. An assembly as recited in claim 30 wherein said displacing means includes a second knob attached to a lower surface of said cover, said second knob being positioned to pass through said second valve aperture to displace said second valve diaphragm when said cover is pressed downwardly.

33. A subcutaneously implantable control assembly for use in an infusion reservoir and pump system, said assembly comprising:

a normally closed first valve having a first valve inlet and a first valve outlet, said first valve being opened to fluid flow therethrough by percutaneous manual manipulation when subcutaneously implanted;

a pump having a pump outlet, a pump inlet in fluid communication with said first valve outlet, and a resilient crown defining at least a portion of a pumping chamber, said pump being manually actuable by the selective application of percutaneous pressure to depress said crown;

a normally closed second valve having a second valve inlet and a second valve outlet, said second valve inlet being in fluid communication with said pump outlet, and said second valve being opened to fluid flow therethrough by percutaneous manual manipulation when subcutaneously implanted;

a generally planar flexible sheet providing a base for said assembly;

a resilient first housing generally attached to and overlying said sheet, said first housing having a first inlet chamber in open communication with said first valve inlet and a first outlet chamber in open communication with a first housing outlet, said first housing being constructed so that a portion of said first outlet chamber generally overlies said first inlet chamber and so that a portion of said first housing outlet generally overlies both said portion of said first outlet chamber and said first inlet chamber, communication between said first inlet chamber and said first outlet chamber being provided by a first valve passageway generally aligned with and positioned below said portion of said first housing outlet; and a first valve stem being attached to and extending downwardly from a first upper ceiling of said first outlet chamber through said first valve passageway and into said first inlet chamber, said first valve stem including a first lower foot which cooperates with a first valve seat provided by said first housing adjacent said first valve passageway to form a first valve seal, sad first valve seal being replaceably broken when a first housing cover overlying said first outlet chamber is resiliently deformed to cause the downward movement of said first valve stem through said first valve passageway.

34. An assembly as recited in claim 33 wherein said resilient crown forms a portion of said first housing, and said pumping chamber is positioned between said first outlet chamber and said first housing outlet.

35. An assembly as recited in claim 34 further including:

a second housing generally attached to and overlying said sheet, said second housing having a second inlet chamber in open communication with a second housing inlet and a second outlet chamber in open communication with said second valve outlet, said second housing being constructed so that a portion of said second outlet chamber generally overlies said second inlet chamber, communication between said second inlet chamber and said second outlet chamber being provided by a second valve passageway generally aligned with and positioned below said portion of said second outlet chamber; and a second valve stem being attached to and extending downwardly from a second upper ceiling of said second outlet chamber through said second valve passageway and into said second inlet chamber.

36. An assembly as recited in claim 35 wherein said first and second housings are constructed of a silicone elastomer material.

37. An assembly as recited in claim 36 wherein said first and second valve stems are constructed of a material different then the material of said housings.

38. An assembly as recited in claim 34 including a rigid needle-guard forming a floor for said pumping chamber, said needle-guard preventing a needle which may be inserted through said crown for passing through said floor of said pumping chamber.

39. An assembly as recited in claim 33 including means for occluding said first housing outlet when said first housing cover is resiliently deformed to cause the downward movement of said first valve stem through said first valve passageway.

40. A valve as recited in claim 1 including means for preventing a reverse flow of fluid through said valve.

41. A valve as recited in claim 40 wherein said preventing means includes a one-way valve situated within said inlet, said one-way valve blocking fluid outflow from said inlet.

42. A process for infusing medications, comprising the steps of:

providing an infusion reservoir and pump system suitable for extended subcutaneous emplacement in the body, the system including a reservoir for storing medication, a catheter for directing the medication to a specific location within the body, and means for pumping and controlling the transfer of medication from the reservoir to the catheter, the pumping and controlling means including a pair of normally closed valves and a pump having a resilient crown overlying a floor plate to define a pumping chamber therebetween, the valves and pump being situated to require the medication to pass through a first valve, then the pump and finally through a second valve before being allowed to enter the catheter;

implanting the system subcutaneously within the body; and transferring the medication from the reservoir to the catheter by applying percutaneous pressure directly to the valves and the resilient crown, the selective application of percutaneous pressure causing the valves to be selectively opened and the pump selectively actuated to effect the flow of medication therethrough.

43. A process as recited in claim 42 wherein percutaneous pressure is selectively applied to the first valve to manipulate and open the first valve for filling a pumping chamber of the pump, and wherein such percutaneous pressure is removed from the first valve to close the same after filling the pumping chamber.

44. A process as recited in claim 43 wherein percutaneous pressure is selectively applied to the second valve after similar percutaneous pressure has been removed from said first valve, to manipulate and open the second valve, and then percutaneous pressure is selectively applied to the pump to flush medication from the pumping chamber through the second valve.

45. A process as recited in claim 44 wherein the percutaneous pressure applied to the second valve is removed prior to removal of the percutaneous pressure on the pump, to avoid the sucking of medication into the pumping chamber through the second valve.

46. A process as recited in claim 42 including a further step of refilling the reservoir by injection subsequent to said step of implanting the system subcutaneously in the body.

47. A process as recited in claim 42 wherein during said implanting step the catheter is situated for delivering medication into the lateral ventricle of the brain.

48. A process as recited in claim 42 wherein during said implanting step the catheter is situated for delivering medication into the lumbar subarachnoid space of the body.

49. A process as recited in claim 42 wherein during said implainting step the reservoir is located adjacent a soft portion of the body so that the reservoir can be percutaneously grasped when subcutaneously implanted.

50. A process as recited in claim 42 wherein during said implanting step the pumping and controlling means is located generally adjacent a bone in the body.

51. A subcutaneously implantable infusion reservoir and pump system, comprising:

means for receiving medication into said system by injection when said system is subcutaneously implanted;

a reservoir securely attached to said receiving means in a manner permitting the subcutaneous transfer of medication from said receiving means to said reservoir, said reservoir including a reservoir outlet;

a catheter for directing the medication to a specific location in a body removed from said reservoir, said catheter having a catheter inlet and being positionable within the body independently of the position of said reservoir;

means for subcutaneously conducting the medication from said reservoir outlet to said catheter inlet; and means for pumping and controlling the flow of medication from said reservoir to said catheter, said pumping and controlling means forming a portion of said conducting means and being independently positionable along the length of said conducting means between said reservoir outlet and said catheter inlet, said pumping and controlline means further being actuated through manual percutaneous pressure when subcutaneously implanted, and being constructed to form a single, integral assembly having an assembly inlet in fluid communication with but separately positionable from said reservoir outlet, and an assembly outlet in fluid communication with but separately positionable from said catheter inlet.

52. A subcutaneously implantable infusion reservoir and pump system, comprising:

means for receiving medication into said system by injection when said system is subcutaneously implanted;

a reservoir securely attached to said receiving means in a manner permitting the subcutaneous transfer of medication from said receiving means to said reservoir, said reservoir including a reservoir outlet;

a catheter for directing the medication to a specific location in a body removed from said reservoir, said catheter having a catheter inlet and being positionable within the body independently of the position of said reservoir;

means for subcutaneously conducting the medication from said reservoir outlet to said catheter inlet; and means for pumping and controlling the flow of medication from said reservoir to said catheter, said pumping and controlling means forming a portion of said conducting means and being independently positionable along the length of said conducting means between said reservoir outlet and said catheter inlet and further being actuated through manual percutaneous pressure when subcutaneously implanted, said pumping and controlling means comprising:

a pump having a pump inlet, a pump outlet, and a resilient crown overlying a floor plate to define a pumping chamber therebetween;

a resiliently flexible housing having an inlet and an outlet;

an inlet chamber within said housing, said inlet chamber being in fluid communication with said inlet;

an outlet chamber within said housing, said outlet chamber being in fluid communication with said outlet and said outlet chamber generally overlying said inlet chamber;

a valve passageway through said housing between said inlet chamber and said outlet chamber, an intermediate portion of said housing generally surrounding said valve passageway and being tapered to form a valve seat; and a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway.

53. A system as recited in claim 51 wherein said pump is interposed between said outlet chamber and said outlet, said pump being defined generally by a hollow void created within said housing, said void forming said pumping chamber.

54. A system as recited in claim 53 wherein said floor plate forms a rigid needle-guard, said needle-guard preventing a needle which may be inserted through said crown from passing through said floor plate.

55. A system as recited in claim 52 including means for occluding said pump outlet and thereby preventing flow through said pump outlet when said upper cover portion of said housing overlying said outlet chamber is resiliently deformed to cause the downward movement of said valve stem through said valve passageway.

56. A subcutaneously implantable infusion reservoir and pump system, comprising:
   means for receiving medication into said system by injection when said system is subcutaneously implanted;
   a reservoir for storing medication injected into said receiving means, said reservoir including a reservoir outlet;
   a normally closed first valve being opened to fluid flow therethrough by percutaneous manual manipulation when subcutaneously implanted, said first valve including:
      a resiliently flexible housing having an inlet in fluid communication with said reservoir outlet, and an outlet,
      an inlet chamber within said housing, said inlet chamber communicating with said inlet,
      an outlet chamber within said housing, said outlet chamer communicating with said outlet and said outlet chamber generally overlying said inlet chamber,
      a valve passageway through said housing between said inlet chamber and said outlet chamber, an intermediate portion of said housing generally surrounding said valve passageway and being tapered to form a valve seat, and
      a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway;
   a pump having a pump inlet in fluid communication with said first valve outlet, a pump outlet, and a resilient crown defining at least a portion of a pumping chamber, said pump being manually actuable by the selective application of percutaneous pressure;
   a normally closed second valve having a second valve inlet in fluid communication with said pump outlet, and a second valve outlet, said second valve being opened to fluid flow therethrough by percutaneous manual manipulation when subcutaneously implanted; and
   a catheter for directing medication to a specific location removed from said reservoir, said catheter having a catheter inlet in fluid communication with said second valve outlet.

57. A system as recited in claim 56 wherein said pump is interposed between said outlet chamber and said outlet, said pump being defined generally by a hollow void created within said housing, said void forming said pumping chamber.

58. A subcutaneously implantable infusion reservoir and pump system, comprising:
   means for receiving medication into said system by injection when said system is subcutaneously implanted;
   a reservoir for storing medication injected into said receiving means, said reservoir including a reservoir outlet;
   a normally closed first valve having a first valve inlet in fluid communication with said reservoir outlet, and a first valve outlet, said first valve being opened to fluid flow therethrough by percutaneous manual manipulation when subcutaneously implanted;
   a pump having a pump inlet in fluid communication with said first valve outlet, a pump outlet, and a resilient crown defining at least a portion of a pumping chamber, said pump being manually actuable by the selective application of percutaneous pressure;
   a normally closed second valve being opened to fluid flow therethrough by percutaneous manual manipulation when subcutaneously implanted, said second valve including:
      a resiliently flexible housing having an inlet in fluid communication with said pump outlet, and an outlet,
      an inlet chamber within said housing, said inlet chamber communicating with said inlet,
      an outlet chamber within said housing, said outlet chamber communicating with said outlet and said outlet chamber generally overlying said inlet chamber,
      a valve passageway through said housing between said inlet chamber and said outlet chamber, an intermediate portion of said housing generally surrounding said valve passageway and being tapered to form a valve seat, and
      a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway; and
   a catheter for directing medication to a specific location removed from said reservoir, said catheter having a catheter inlet in fluid communication with said second valve outlet.

59. An infusion reservoir and pump system for the administration of medication to a human body, said system comprising:

means for subcutaneously receiving the medication into said system by injection, said receiving means including a self-sealing dome overlying a rigid needle-shield to define an injection chamber therebetween, said needle-shield having a shield outlet passageway to permit the medication to exit said injection chamber;

a variable capacity reservoir securely attached to said receiving means, said reservoir including a reservoir inlet and a reservoir outlet, said reservoir inlet cooperating with said needle-shield and said shield outlet passageway to permit the transfer of the medication from said receiving means to said reservoir when the fluid pressure of the medication in said injection chamber exceeds the fluid pressure of the medication in said reservoir;

a catheter for directing the medication to a specific location in the body, said catheter having a catheter inlet;

means for conducting the medication of said reservoir outlet to said catheter inlet;

a one-way valve situated within said conducting means, said one-way valve causing the flow of the medication through said conducting means to be unidirectional;

a pump forming a portion of said conducting means, said pump including a resilient crown overlying a floor plate to define a pumping chamber therebetween, said pump having a pump inlet which receives medication from said reservoir and a pump outlet which can be placed in fluid communication with said catheter inlet; and means for preventing the unintended transfer of medication from said reservoir through said conducting means to said catheter, said preventing means cooperating with said pump to require at least a two-step procedure to transfer a measured quantity of the medication from said reservoir through said pump to said catheter inlet, said preventing means including a normally closed first valve forming a portion of said conducting means between said reservoir and said pump, said first valve including a rigid first housing and a resilient first cover, sad first housing forming a first lower inlet chamber which houses a flexible first valve diaphragm resiliently biased to close a first valve aperture through said first housing, and said first cover including means for displacing said first valve diaphragm away from said first valve aperture to open said first valve.

60. A system as recited in claim 59 wherein said reservoir inlet is resiliently biased to be normally situated adjacent a solid flat undersurface of said needle-shield, said reservoir inlet separating from said undersurface when the fluid pressure within said injection chamber is greater than the fluid pressure within said reservoir to allow the medication in said injection chamber to flow through said shield outlet passageway to said reservoir inlet.

61. A system as recited in claim 59 wherein said reservoir inlet cooperates with said receiving means to prevent the medication stored in said reservoir from flowing into said receiving means.

62. A system as recited in claim 59 wherein said one-way valve is situated within said reservoir outlet.

63. A system as recited in claim 62 wherein said one-way valve includes a rigid encasement which protects a resilient one-way valve membrane situated within said encasement.

64. A system as recited in claim 59 further including a flexible tube extending from said reservoir outlet into said reservoir to channel the medication through said reservoir outlet notwithstanding a collapse of said reservoir about said reservoir outlet.

65. A system as recited in claim 59 wherein said catheter is sized for insertion into the lumbar subarachnoid space of the body.

66. A system as recited in claim 59 wherein said catheter is sized for insertion into the lateral ventricle of a brain.

67. A system as recited in claim 59 wherein said catheter is constructed of a radiopaque, barium-impregnated silicone elastomer material.

68. A system as recited in claim 50 wherein said pump and said preventing means are constructed to form a single, integral control assembly unit which shares a common base, said control assembly unit having a unit inlet in fluid communication with said reservoir outlet and a unit outlet in fluid communication with said catheter inlet.

69. A system as recited in claim 59 wherein said displacing means includes a first knob attached to a lower surface of said first cover, said first knob being positioned to pass through said first valve aperture to displace said fist valve diaphragm when said first cover is pressed downwardly, the displacement of said first valve diaphragm allowing the medication to pass from said first lower inlet chamber through said first valve aperture into a first upper outlet chamber, said first upper outlet chamber being in open communication with said pump inlet.

70. A system as recited in claim 59 wherein said preventing means further includes a normally closed second valve forming a portion of said conducting means between said pump and said catheter inlet.

71. A system as recited in claim 70 wherein said second valve includes a rigid second housing and a resilient second cover, said second housing forming a second lower inlet chamber which houses a flexible second valve diaphragm resiliently biased to close a second valve aperture through said second housing, said second cover including means for displacing said second valve diaphragm away from said second valve aperture to open said second valve.

72. An infusion reservoir and pump system for the administration of medication to a human body, said system comprising:

means for subcutaneously receiving the medication into said system by injection, said receiving means including a self-sealing dome overlying a rigid needle-shield to define an injection chamber therebetween, said needle-shield having a shield outlet passageway to permit the medication to exit said injection chamber;

a variable capacity reservoir securely attached to said receiving means, said reservoir including a reservoir inlet and a reservoir outlet, said reservoir inlet cooperating with said needle-shield and said shield outlet passageway to permit the transfer of the medication from said receiving means to said reservoir when the fluid pressure of the medication in said injection chamber exceeds the fluid pressure of the medication in said reservoir;

a catheter for directing the medication to a specific location in the body, said catheter having a catheter inlet;

means for conducting the medication from said reservoir outlet to said catheter inlet;

a one-way valve situated within said conducting means, said one-way valve causing the flow of the medication through said conducting means to be unidirectional;

a pump forming a portion of said conducting means, said pump including a resilient crown overlying a floor plae to define a pumping chamber therebetween, said pump having a pump inlet which receives medication from said reservoir and a pump outlet which can be placed in fluid communication with said catheter inlet; and means for preventing the unintended transfer of medication from said reservoir through said conducting means to said catheter, said preventing means cooperating with said pump to require at least a two-step procedure to transfer a measured quantity of the medication from said reservoir through said pump to said catheter inlet, said preventing means including a normally closed first valve forming a portion of said conducting means between said reservoir and said pump, and a normally closed second valve forming a portion of said conducting means between said pump and said catheter inlet, said second valve including a rigid housing and a resilient cover, said housing forming a lower inlet chamber which houses a flexible valve diaphragm resiliently biased to close a valve aperture through said housing, and said cover including means for displacing said valve diaphragm away from said valve aperture to open said second valve.

73. An infusion reservoir and pump system for the administration of medication to a human body, said system comprising:

means for subcutaneously receiving the medication into said system by injection, said receiving means including a self-sealing dome overlying a rigid needle-shield to define an injection chamber therebetween, said needle-shield having a shield outlet passageway to permit the medication to exit said injection chamber;

a variable capacity reservoir securely attached to said receiving means, said reservoir including a reservoir inlet and a reservoir outlet, said reservoir inlet cooperating with said needle-shield and said shield outlet passageway to permit the transfer of the medication from said receiving means to said reservoir when the fluid pressure of the medication in said injection chamber exceeds the fluid pressure of the medication in said reservoir;

a catheter for directing the medication to a specific location in the body, said catheter having a catheter inlet;

means for conducting the medication from said reservoir outlet to said catheter inlet;

a one-way valve situated within said conducting means, said one-way valve causing the flow of the medication through said conducting means to be unidirectional;

a pump forming a portion of said conducting means, said pump including a resilient crown overlying a floor plate to define a pumping chamber therebetween, said pump having a pump inlet which receives medication from said reservoir and a pump outlet which can be placed in fluid communication with said catheter inlet; and means for preventing the unintended transfer of medication from said reservoir through said conducting means to said catheter, said preventing means cooperating with said pump to require at least a two-step procedure to transfer a measured quantity of the medication from said reservoir through said pump to said catheter inlet, said preventing means including:

a resiliently flexible housing having an inlet and an outlet, an inlet chamber within said housing, said inlet chamber being in open communication with said inlet;

an outlet chamber within said housing, said outlet chamber being in open communication with said outlet and said outlet chamber generally overlying said inlet chamber, a valve passageway through said housing between said inlet chamber and said outlet chamber, an intermediate portion of said housing generally surrounding said valve passageway, said intermediate portion of said housing being tapered to form a valve seat, and a valve stem constructed of a material different from the material of said housing, said valve stem being attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway.

74. A system as recited in claim 73 wherein said housing is constructed of a silicone elastomer material.

75. A system as recited in claim 74 wherein said valve stem is constructed of a polypropylene material.

76. A system as recited in claim 73 wherein said inlet chamber is defined, in part, by a reinforced sheet underlying said housing.

77. A system as recited in claim 73 including an integral rigid connector defining said outlet.

78. A system a recited in claim 73 wherein said pump is interposed between said outlet chamber and said outlet, said pump being defined generally by a hollow void created within said housing, said void forming said pumping chamber.

79. A system as recited in claim 78 wherein said floor plate forms a rigid needle-guard, said needle-guard preventing a needle which may be inserted through said crown from passing through said floor plate.

80. A system as recited in claim 73 including means for occluding said pump outlet and thereby preventing flow through said pump outlet when said upper cover portion of said housing overlying said outlet chamber is resiliently deformed to cause the downward movement of said valve stem through said valve passageway.

81. A system as recited in claim 73 wherein said one-way valve is situated within said inlet.

82. An infusion reservoir and pump system for the administration of medications, said system comprising:

means for receiving the medications into said system by injection;

a reservoir securely attached to said receiving means in a manner permitting the transfer of the medications from said receiving means to said reservoir, said reservoir including a reservoir inlet and a reservoir outlet;

a normally closed first valve having a first valve inlet and a first valve outlet, said first valve inlet being in open communication with said reservoir outlet;

a pump having a pump inlet and a pump outlet, said pump inlet being in open communication with said first valve outlet;

a normally closed second valve having a second valve inlet and a second valve outlet, said second valve inlet being in open communication with said pump outlet; and a catheter having a catheter inlet in open communication with said second valve outlet;

said first valve, said pump and said second valve being combined to form a single, integral control assembly unit, said unit having a unit inlet generally corresponding to said first valve inlet and a unit outlet generally corresponding to said second valve outlet, said unit further comprising a resiliently rigid housing and a resiliently flexible cover over said housing, said housing and said cover cooperating to substantially enclose and define a fluid flow passageway through said unit, said housing forming a first lower inlet chamber in said first valve, said first lower inlet chamber supporting a first valve diaphragm resiliently biased to close a first valve aperture through said housing.

83. A system as recited in claim 82 wherein said housing forms a second lower inlet chamber in said second valve, said second lower inlet chamber supporting a second valve diaphragm resiliently biased to close a second valve aperture through said housing.

84. A system as recited in claim 83 wherein said cover includes means for displacing said first valve diaphragm away from said first valve aperture and said second valve diaphragm away from said second valve aperture.

85. A system as recited in claim 84 wherein said displacing means includes a first knob attached to a lower surface of said cover, said first knob being positioned to pass through said first valve aperture to displace said first valve diaphragm when said cover is pressed downwardly.

86. A system as recited in claim 84 wherein said displacing means includes a second knob attached to a lower surface of said cover, said second knob being positioned to pass through said second valve aperture to displace said second valve diaphragm when said cover is pressed downwardly.

87. An infusion reservoir and pump system for the administration of medications, said system comprising:

means for receiving the medications into said system by injection;

a reservoir securely attached to said receiving means in a manner permitting the transfer of the medications from said receiving means to said reservoir, said reservoir including a reservoir inlet and a reservoir outlet;

a normally closed first valve having a first valve inlet and a first valve outlet, said first valve inlet being in open communication with said reservoir outlet;

a pump having a pump inlet and a pump outlet, said pump inlet being in open communication with said first valve outlet;

a normally closed second valve having a second valve inlet and a second valve outlet, said second valve inlet being in open communication with said pump outlet; and a catheter having a catheter inlet in open communication with said second valve outlet;

said first valve, said pump and said second valve being combined to form a single, integral control assembly unit, said unit having a unit inlet generally corresponding to said first valve inlet and a unit outlet generally corresponding to said second valve outlet, said unit further comprising:

a generally planar flexible sheet providing a base for said unit, a resilient first housing generally attached to and overlying said sheet, said first housing having a first inlet chamber in open communication with said unit inlet and a first outlet chamber in open communication with a first housing outlet, said first housing being constructed so that a portion of said first outlet chamber generally overlies said first inlet chamber and so that a portion of said first housing outlet generally overlies both said portion of said first outlet chamber and said first inlet chamber, said first inlet chamber and said first outlet chamber being connected to one another by a first valve passageway generally aligned with and positioned below said portion of said first housing outlet, and a first valve stem constructed of a material different than the material of said first housing, said first valve stem being attached to and extending downwardly from a first upper ceiling of said first outlet chamber through said first valve passageway and into said inlet chamber, said first valve stem including a first lower foot which cooperates with a first valve seat provided by said first housing adjacent said first valve passageway to form a first valve seal, said first valve seal being replaceably broken when a first housing cover overlying said first outlet chamber is resiliently deformed to cause the downward movement of said first valve stem through said first valve passageway.

88. A system as recited in claim 87 wherein said unit further includes a pumping chamber forming a void within said first housing, said pumping chamber being positioned between said first outlet chamber and said first housing outlet.

89. A system as recited in claim 88 wherein said unit further includes:

a second housing generally attached to and overlying said sheet, said second housing having a second inlet chamber in open communication with a second housing inlet and a second outlet chamber in open communication with said unit outlet, said second housing being constructed so that a portion of said second outlet chamber generally overlies said second inlet chamber, said second inlet chamber and said second outlet chamber being connected to one another by a second valve passageway generally aligned with and positioned below said portion of said second outlet chamber; and a second valve stem constructed of a material different than the material of said second housing, said second valve stem being attached to and extending downwardly from a second upper ceiling of said second outlet chamber through said second valve passageway and into said second inlet chamber.

90. A system as recited in claim 89 wherein said first and second housings are constructed of a silicone elastomer material.

91. A system as recited in claim 90 wherein said first and second valve stems are constructed of a polypropylene material.

92. A system as recited in claim 88 including a rigid needle-guard forming a floor for said pumping chamber, said needle-guard preventing a needle which may be inserted through said first housing from passing through said floor of said pumping chamber.

93. A system as recited in claim 87 including means for occluding said first housing outlet when said first housing cover is resiliently deformed to cause the downward movement of said first valve stem through said first valve passageway.

94. A valve and pump device for use in an infusion reservoir and pump system, said device comprising:
an inlet;
an outlet;
a normally closed first valve situated generally adjacent and in fluid communication with said inlet;
a normally closed second valve situated generally adjacent and in fluid communication with said outlet;
a pump interposed between and in fluid communication with said first valve and said second valve, said device being constructed of materials suitable for subcutaneous implantation over extended periods of time;
a resiliently rigid housing and resiliently flexible cover over said housing, said housing and said cover cooperating to substantially enclose and define a fluid flow passageway through said device, said housing forming a first lower inlet chamber for said first valve, said first lower inlet chamber supporting a first valve diaphragm resiliently biased to close a first valve aperture through said housing, and a second lower inlet chamber for said second valve, said second lower inlet chamber supporting a second valve diaphragm resilient biased to close a second valve aperture through said housing, said cover including means for displacing said first valve diaphragm away from said first valve aperture and said second valve diaphragm away from said second valve aperture.

95. A device as recited in claim 94 wherein said displacing means includes a first knob attached to a lower surface of said cover, said first knob being positioned to pass through said first valve aperture to displace said first valve diaphragm when said cover is pressed downwardly.

96. A device as recited in claim 94 wherein said displacing means includes a second knob attached to a lower surface of said cover, said second knob being positioned to pass through said second valve aperture to displace said second valve diaphragm when said cover is pressed downwardly.

97. A valve and pump device for use in an infusion reservoir and pump system, said device comprising:
an inlet;
an outlet;
a normally closed first valve situated generally adjacent and in fluid communication with said inlet;
a normally closed second valve situated generally adjacent and in fluid communication with said outlet;
a pump interposed between and in fluid communication with said first valve and said second valve, said device being constructed of materials suitable for subcutaneous implantation over extended periods of time;
a generally planar flexible sheet providing a base for said device;
a first housing generally attached to and overlying said sheet, said first housing having a first inlet chamber in open communication with said inlet and a first outlet chamber in open communication with a first housing outlet, said first housing being constructed so that a portion of said first outlet chamber generally overlies said first inlet chamber and so that a portion of said first housing outlet generally overlies both said portion of said first outlet chamber and said first inlet chamber, said first inlet chamber and said first outlet chamber being connected to one another by a first valve passageway generally aligned with and positioned below said portion of said first housing outlet; and
a first valve stem constructed of a material different than the material of said first housing, said first valve stem being attached to and extending downwardly from a first upper ceiling of said first outlet chamber through said first valve passageway and into said first inlet chamber, said first valve stem including a first lower foot which cooperates with a first valve seat provided by that portion of said first housing generally surrounding said first valve passageway to form a first valve seal therebetween, said first valve seal being replaceably broken when a first housing cover overlying said first outlet chamber is resiliently deformed to cause the downward movement of said first valve stem through said first valve passageway.

98. A device as recited in claim 97 wherein said pump includes a pumping chamber forming a void within said first housing, said pumping chamber being positioned between said first outlet chamber and said first housing outlet for receiving fluid from said first outlet chamber and exhausting the fluid into said first housing outlet.

99. A device as recited in claim 98 including:
a second housing generally attached to and overlying said sheet, said second housing having a second inlet chamber in open communication with said first housing outlet and a second outlet chamber in open communication with said outlet, said second outlet chamber generally overlying said second inlet chamber, said second inlet chamber and said second outlet chamber being connected to one another by a second valve passageway; and
a second valve stem constructed of a material different from the material of said second housing, said second valve stem being attached to and extending downwardly from a second upper ceiling of said second outlet chamber through said second valve passageway and into said second inlet chamber, said second valve stem including a second lower foot which cooperates with a second valve seat provided by that portion of said second body generally surrounding said second valve passageway to form a second valve seal therebetween, said second valve seal being replaceably broken when a second housing cover overlying said second outlet chamber is resiliently deformed to cause the downward movement of said second valve stem through said second valve passageway.

100. A device as recited in claim 99 wherein said first and second housings are constructed of a silicone elastomer material and said first and second valve stems are constructed of a polypropylene material.

101. A device as recited in claim 97 including an integral, rigid connector defining said outlet.

102. A device as recited in claim 98 including a rigid needle-guard forming a floor for said pumping chamber, said needle-guard preventing a needle which may be inserted through said first housing from passing through said floor of said pumping chamber.

103. A device as recited in claim 98 including means for occluding said first housing outlet when said first housing cover is resiliently deformed to cause the downward movement of said first valve stem through said first valve passageway.

104. A process for infusing medications, comprising the steps of:

providing an infusion reservoir and pump system constructed of materials suitable for extended subcutaneous emplacement in the body, the system including a reservoir for receiving and storing the medications, a catheter for directing the medications to a specific location within the body, a fluid flow conduit connecting the reservoir and the catheter, and a pump and valving arrangement forming a portion of the fluid flow conduit;

implanting the system subcutaneously in the body; and transferring the medications from the reservoir through the fluid flow conduit to the catheter for delivery of the medications to the body, the flow of the medications through the fluid flow conduit being controlled by the pump and valving arrangement;

wherein said pump and valving arrangement is located so that it can be percutaneously manipulated when subcutaneously implanted to pump measured quantities of the medications through the system during said transferring step, and includes a pair of normally closed valves and a pump, and during said transferring step the valves are manipulated to cause each to open for permitting fluid flow therethrough, and the pump is similarly manipulated to cause a pumping chamber within the pump to be evacuated for propelling the medications through the pump and valving arrangement;

said step of providing the system includes situating the pair of valves within the fluid flow conduit to require the medications to pass through a first valve, then the pump and finally a second valve before being allowed to enter said catheter during said transferring step; and said transferring step requiring the first valve to be manually manipulated percutaneously to open and permit the medications to flow from the reservoir to fill the pumping chamber.

105. A process as recited in claim 104 including a further step of refilling the reservoir by injection subsequent to said step of implanting the system subcutaneously in the body.

106. A process as recited in claim 104 wherein during said implanting step the catheter is situated for delivering the medications into the lateral ventricle of the brain.

107. A process as recited in claim 104 wherein during said implanting step the catheter is situated for delivering the medications into the lumbar subarachnoid space of the body.

108. A process as recited in claim 104 wherein during said implanting step the reservoir is located adjacent a soft portion of the body so that the reservoir can be percutaneously grasped when subcutaneously implanted.

109. A process as recited in claim 104 wherein during said implanting step the pump and valving arrangement is located generally adjacent a bone in the body.

110. A process as recited in claim 104 wherein said transferring step requires the second valve and the pump to be manually manipulated percutaneously to simultaneously open the second valve and flush the pumping chamber to direct the medications to the catheter.

* * * * *

UNITED STATES PATENT AND TRADEMARK OFFICE
CERTIFICATE OF CORRECTION

PATENT NO. : 4,588,394

DATED : May 13, 1986

INVENTOR(S) : Rudolf R. Schulte; Gary P. East; Alfons Heindle

It is certified that error appears in the above-identified patent and that said Letters Patent is hereby corrected as shown below:

In Column 2, lines 36 & 37, please delete the word "explacement" and insert therefor --emplacement--.

In Column 3, line 17, please delete the word "deliberated" and insert therefor --deliberate--.

In Column 5, line 65, please delete the word "field" and insert therefor --fluid--.

In Column 9, line 9, please delete the word "haing" and insert therefor --having--.

In Column 9, line 14, please delete the word "the" and insert therefor --that--.

In Column 10, line 4, please delete the word "silicon" and insert therefor --silicone--.

In Column 10, line 6, please delete the word "silicon" and insert therefor --silicone--.

In Column 11, line 41, please delete the word "be".

UNITED STATES PATENT AND TRADEMARK OFFICE
CERTIFICATE OF CORRECTION

PATENT NO. : 4,588,394  
DATED : May 13, 1986  
INVENTOR(S) : Rudolf R. Schulte; Gary P. East; Alfons Heindle It is certified that error appears in the above-identified patent and that said Letters Patent is hereby corrected as shown below:

In Column 12, line 6, please delete the word "chamber" and insert therefor --cover--.

In Column 13, line 1, please delete the word "fluids" and insert therefor --fluid--.

In Column 15, line 50, please delete the word "seat" and insert therefor --seal--.

In Column 15, line 63, please insert the word --stem-- before the number "228'".

In Column 17, line 34, please delete the word "closes" and insert therefor --closed--.

In Column 19, line 45, please delete the word "bariumimpregnated" and insert therefor --barium-impregnated--.

In Column 20, line 43, please delete the word "be" and insert therefor --by--.

In Column 22, line 15, please delete the word "sad" and insert therefore --said--.

UNITED STATES PATENT AND TRADEMARK OFFICE
CERTIFICATE OF CORRECTION

PATENT NO. : 4,588,394

DATED : May 13, 1986

INVENTOR(S) : Rudolf R. Schulte; Gary P. East; Alfons Heindle

It is certified that error appears in the above-identified patent and that said Letters Patent is hereby corrected as shown below:

In Column 22, line 52, please delete the word "for" and insert therefor --from--.

In Column 24, line 14, please delete the word "controlline" and insert therefor --controlling--.

In Column 25, line 42, please delete the word "chamer" and insert therefor --chamber--.

In Column 27, line 46, please delete the word "sad" and insert therefor --said--.

In Column 28, line 19, please delete the number "50" and insert therefor --59--.

In Column 28, line 30, please delete the word "fist" and insert therefor --first--.

In Column 29, line 12, please delete the word "plae" and insert therefor --plate--.

Signed and Sealed this

Twelfth Day of August 1986

[SEAL]

Attest:

DONALD J. QUIGG

Attesting Officer

Commissioner of Patents and Trademarks